Figure 1A:
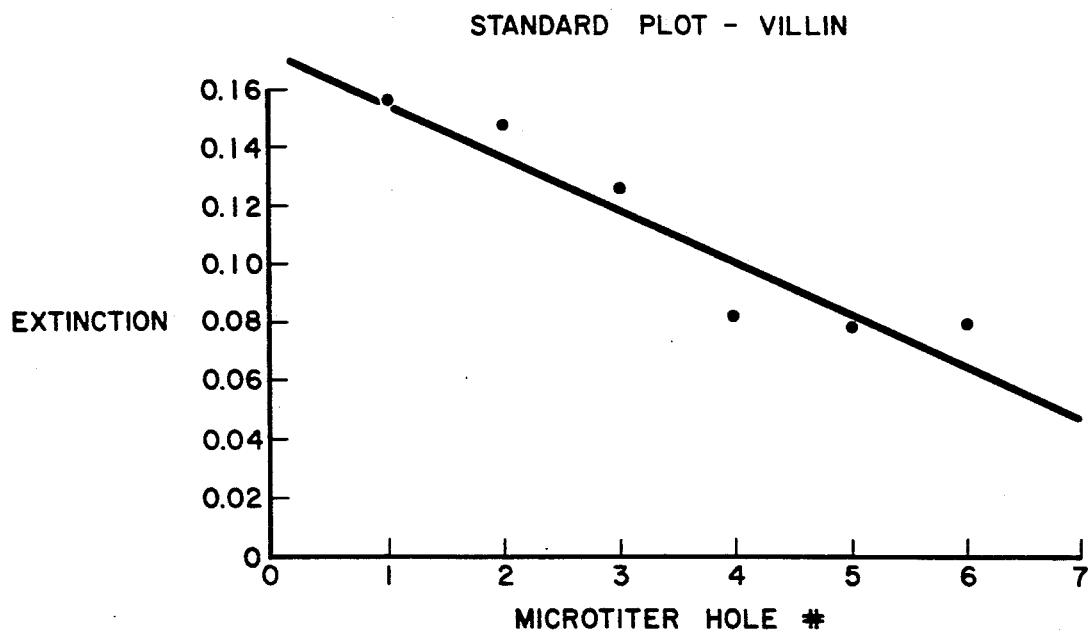

United States Patent [19]

Drenckhahn

[11] Patent Number: 5,141,876
[45] Date of Patent: Aug. 25, 1992

[54] METHOD AND COMPOSITION FOR THE DETERMINATION OF KIDNEY DAMAGES

[76] Inventor: Detlef Drenckhahn, Ulmenweg 30, D-3550 Marburg, Fed. Rep. of Germany

[21] Appl. No.: 312,488

[22] Filed: Feb. 21, 1989

[30] Foreign Application Priority Data

Feb. 22, 1988 [DE] Fed. Rep. of Germany ....... 3805447

[51] Int. Cl.⁵ .......................................... G01N 33/543
[52] U.S. Cl. ..................... 436/518; 435/7.5; 435/7.92; 436/811
[58] Field of Search ...................... 435/7.5, 7.92, 7.93, 435/7.94, 975; 436/531, 523, 528, 530, 541, 545, 547, 548, 804, 808; 530/387

[56] References Cited

U.S. PATENT DOCUMENTS 4,465,776  8/1984  Cidlowski et al. .................. 436/504
4,731,326  3/1988  Thompson et al. ................. 435/7.25

OTHER PUBLICATIONS

Rodman, J. S. et al., "Cytoskeletal Proteins of the Rat Kidney Proximal Tubule Brush Border", *European Journal of Cell Biology* (1986), vol. 42, pp. 319-327.

Bretscher, A. et al., "Villin Associates with Specific Microfilamentous Structures as seen by Immunofluorescence Microscopy on Tissue Sections and Cells Microinjected with Villin", *Experimental Cell Research* (1981), col. 135, pp. 213-219.

Bretscher, A. et al., "Fimbrin, a New Microfilament-Associated Protein Present in Microvilli and Other Cell Surfaces", *Journal of Cell Biology* (1980), vol. 86, pp. 335-340.

Bretscher, A. et al., "Villin is a Major Protein of the Microvillus Cytoskeletono Which Binds Both G and F Actin in a Calcium-Dependent Manner", *Cell* (1980), vol. 20, pp. 839-847.

Drenckhahn, D. et al., "Evidence for the Association of Villin with Core Filaments and Rootlets of Intestinal Epithelial Microvilli", *Cell and Tissue Research* (1983), vol. 228, pp. 409-414.

ICN Biomedicals Inc. Reference Catalog 1987, pp. 1B-1, 1B-2, 1B-49.

Bretscher et al., Proc. Natl. Acad. Sci. USA 76(1979), pp. 2321-2325.

Kohler and Milstein, "Continuous Cultures of Fused Cells Secreting Antibody of Predefined Specificity", Nature 256: 495-497 (Aug. 7, 1975).

*Primary Examiner*—Esther L. Kepplinger
*Assistant Examiner*—Carol E. Bidwell
*Attorney, Agent, or Firm*—Beveridge, DeGrandi & Weilacher

[57] ABSTRACT

The invention refers to a method as well as a composition for the quantitative determination of kidney damages by the application of polyclonal and monoclonal antibodies against villin and/or fimbrin appearing in the urine as soon as damages of the kidney, for example reactions of rejection in case of a transplanted kidney or tubular inflammations, are occurring.

10 Claims, 2 Drawing Sheets

METHOD AND COMPOSITION FOR THE DETERMINATION OF KIDNEY DAMAGES

FIELD OF THE INVENTION

Subject of the invention is a method for the determination of kidney damages in which polyclonal or monoclonal antibodies are brought into contact with proteins present in the kidney and the reaction product received is thereafter subjected to an immunological identification as well as a composition to carry out this method.

Usually kidney damages first become noticeable by injuries of the parenchyma occurring, for example, where, in case of a healthy kidney, kidney damaging drugs such as phenacetin are taken continuously or, in case of a transplanted kidney, no immune-suppressive drug is taken. To this extent the early detection of parenchyma injuries of the kidney is an important medical problem.

DESCRIPTION OF THE PRIOR ART

At present, mainly three examination methods are applied to determine parenchyma injuries of the kidney:
  a. The classical method is to take tissue specimen, by biopsy, from the kidney. However, there are complications attached to this invasive method and it is thus applied only in exceptional cases.
  b. The activity of tissue enzymes in the urine is determined. This clinical test, however, is highly restricted as to its evidence, since it is not meant to provide for a reliable localization of the place of damage in the kidney and the activity of the enzymes in the urine is influenced by numerous external factors. This test is too unspecific already from a qualitative point of view.
  c. Furthermore it was tried to detect kidney damages the immunological way. To do so, monoclonal antibodies were applied against unknown or insufficiently characterized kidney proteins increased quantities of which are excreted with urine. This method may, at best, be considered a rough qualitative method for the determination of kidney damages, as the antibodies directed against proteins are not isolated and consequently not employed with respect to the quantitative calibration of the measured values. In this respect, this method is not at all meant to provide for quantitative statements which are necessary to estimate the degree of severity of a kidney damage.

SUMMARY OF THE INVENTION

The invention is, therefore, aimed to improve the method of the kind mentioned above in a way that minor or enlarging kidney damages may quantitatively be determined.

The invention is furthermore aimed at providing a composition for the performance of said method.

The problem is solved in that such antibodies are used which are specific against the proteins fimbrin or villin.

Surprisingly enough it was found out now that the proteins villin and fimbrin, being two molecular defined proteins of the proximal renal tubule epithelium, may practically quantitatively be taken as measure for a kidney damage. Then these proteins in the urine can quantitatively be determined. For both proteins are increasingly excreted in case of a damage of the kidney which is affecting the proximal tubulus or including it. Thus, according to the invention a non-invasive diagnostic method is available by which kidney damages caused by, for example, circulatory disturbances, imminent acute renal failure or imminent rejection of a transplanted organ can quantitatively be determined at an early stage. Based on the method according to the invention statements with respect to the following clinical questions can be made, to wit a. localization of kidney damage in the proximal tubulus,
  b. judgement on the degree of severity of the cell injury,
  c. reactivity of the kidney damage to therapeutical measures, and
  d. estimation of the risk of treating patients suffering from a kidney disease and patients with a transplanted kidney with drugs having kidney damaging side effects.

The proteins villin and fimbrin can simply be identified in the urine they are excreted with. Usually only about 0.1 ml of patient's excreted urine is required. To this extent the identification remains without damaging or toxic effects on the patient, since the excreted urine is analyzed in vitro.

The proteins villin and fimbrin can be determined in purified form. This allows an exact determination of the measured values, i.e. the proteins fimbrin and villin can exactly and quantitatively be identified in the urine, thus providing a parameter for the degree of severity of the damaging of the renal tubuli. An advantage of the method according to the invention is a calibration of the applied reagent in order to quantitatively identify the content of the proteins villin and/or fimbrin in the urine.

A typical, simple method for the quantitative identification of the proteins villin and fimbrin in the urine comprises the following characteristics: The proteins villin and fimbrin are isolated by known ways from the intestinal epithelium of chicken or pig. This method is described by A. Bretscher and K. Weber in Proc. Natl. Acad. Sci. U.S.A. 76 (1979), pages 2321-2325 or J. Cell. Biol. 86 (1980) pages 335-340 or D. Drenckhahn et al. in Cell. Tiss. Res. 228 (1983). The isolation methods outlined therein are explicitly incorporated by reference.

It is possible to isolate these proteins in the same way from the intestinal epithelium of surgically removed pieces of the intestines of the human body.

Antibodies against fimbrin and/or villin can be produced either according to the literature references cited above or also according to generally known methods. Such methods are, for example, described in the monograph by R. J. Mayer and J. H. Walker entitled "Immunochemical methods in the biological sciences: Enzymes and proteins" published by Academic Press, London (1980). For example, the isolated proteins in quantities of 50-100 μg, with or without the complete or incomplete adjuvant according to Freund, are injected into the dorsal skin or peritoneal cavity of rabbits or guinea pigs. In intervals of three weeks the same quantity of proteins is injected again. After the third or any later injection good titers of polyclonal antibodies are obtained which are chemically purified according to common standard methods and tested as to their specificity. Such a method was described in the above-mentioned publications by Drenckhahn et al, 1983, or Bretscher and Weber, 1979, 1980 or by Talian et al in J. Cell. Biol. 97 (1983), pages 1277-1282 which are incorporated by reference.

Besides polyclonal antibodies, monoclonal antibodies produced in mice and rats according to also commonly known methods (cf. the publications by J. H. Peters et al, "Monoklonale Antikörper: Herstellung und Charakterisierung", published by Springer, Berlin (1985)) may be applied as well.

Such monoclonal antibodies against villin are described in the European patent application 206 849 and are already offered on the market by Messrs. Dianova, Hamburg, for the histological diagnosis of tumours of the intestine in which villin is released as well.

According to the invention polyclonal or monoclonal antibodies against the proteins villin and/or fimbrin are bound to the surface of reaction carriers. "Binding" in this context means either a physical adsorption of the antibodies to a substrate or a chemical covalent binding of these antibodies to the substrate.

Filter materials, materials of reaction vessels such as microtiter plates, column chromatography materials such as sepharose and the like may serve as reaction carriers. The antibodies are brought into contact with the substrate material in an aqueous solution preferably in an aqueous buffer solution, until an adsorption balance is reached. This balance setting is temperature dependent and takes about 3 hours at approx. 21° C. and about 12 hours at 4° C.

As substrate material a synthetic material, especially polystyrene, is preferred which is usually used for the manufacture of microtiter plates.

Upon completion of the binding reaction and for purposes of saturation of empty protein binding sites the adsorbed antibodies are treated with protein solutions, for example albumin solutions, gelatin solutions or skimmed milk, if necessary by adding a saline solution and/or detergents.

Thereafter the so treated antibody coatings are washed several times, whereupon treatment with a urine specimen can be effected.

Incubation with urine is made until a reaction balance between the antibodies and the proteins villin and/or fimbrin is reached. The incubation process preferably takes approx. 30-90 minutes. Thereafter the urine is removed and, where microtiter plates are used, the wells are filled again with the aforementioned washing solution which is changed several times in certain intervals.

As a second step, the so reached antibody protein binding complex is thereafter subjected to an immunologic quantification reaction.

To conduct this quantification reaction occurring in the second step of the process the substrate adhering antibody protein binding complex is again treated with antibodies against villin or fimbrin.

Where in the first step of the process a polyclonal antibody was used, either the same polyclonal antibody or a monoclonal antibody against villin or fimbrin is applied in the second step.

If, however, according to a second embodiment a monoclonal antibody is used in the first step of the process then, in the second step, either a polyclonal or a second monoclonal antibody different from the first antibody can be applied as an antibody which is directed against another binding site of the protein molecule.

Hereinafter the antibody used in this second step of the process is referred to as "second antibody".

According to the invention the wells of the microtiter plates are also filled and incubated for approx. 30-90 minutes with a solution containing this second antibody. Thereafter the second antibody solution is removed whereupon the wells are washed with a washing solution. Left with the substrate remains a complex consisting of the first antibody, the bound proteins villin and fimbrin and the second antibody, hereinafter referred to as "quantification complex".

This quantification complex can be subjected to a quantification reaction in multiple ways:

According to a first embodiment, the second antibody is subjected to a covalent linkage with enzymes, for example peroxidase, alkaline phosphatase, glucoseoxidase or beta-galactosidase. The volume of the enzyme-labelled second antibodies bound in the quantification complex can then quantitatively be determined by an enzyme colour reaction. Such quantification reactions are known and applicable enzymes as well as typical enzyme colour reactions were described by L. A. Sternberger in "Immunocytochemistry", Third Edition, published by John Wiley & Sons, New York (1986) or by W. D. Kuhlmann in the monograph "Immunoenzyme techniques in cytochemistry", published by Verlag Chemie, Weinheim (1984) which are incorporated by reference.

According to a second embodiment, the second antibodies can be radiolabelled according to commonly known methods, for example with iodine 125. For these purposes radioactive marking kits and substances are used and supplied by, for example, NEN in Dreieich (Germany).

The amount of the bound second antibodies can thus directly and quantitatively be determined by means of a particle counter or a radiation counter.

In a third embodiment of the quantification reaction, the complex can be treated with a third antibody which is specific against the bound second antibody. For these purposes, for example, antibodies against mouse immunoglobulins or rabbit immunoglobulins may be used. Such antibodies are available on the market in labelled form with enzymes or radio-isotopes and are, for example, distributed by Messrs. Dianova, Hamburg, Messrs. Janssen, Belgium, or NEN in Dreieich (Germany). The next step is the quantification process already mentioned above. In said step either the colour reaction or the radioactive radiation are quantitatively determined.

These third antibodies in their non-labelled form may also serve as cross-linking antibodies forming enzyme-anti-enzyme immune complexes which, if at all, are introduced in a fourth incubation step. These indirect immunoglobulin identifications are known from literature as well and can be found, for example, in Sternberger's aforementioned monograph which is incorporated by reference. By the way, the enzyme-anti-enzyme immune complexes are also available on the market and are distributed, for example, by Messrs. Dianova, Hamburg, or Messrs. Janssen, Belgium.

In a fourth quantification reaction described hereinafter in detail and preferred so far, quantification of villin and fimbrin in the urine is made by covalent linkage of the second antibodies with biotin. Biotin linkage is made to the second antibody in accordance with known procedures as, for example, described by N. H. Heggeness et al in Cell. Biol. 73 (1977), pages 783-788 and incorporated by reference. For this purpose, for example, biotin-N-hydroxysuccinimid-ester is used which is distributed by Calbiochem-Hoechst.

The second antibodies having a biotin label and bound in the quantification complex are quantified by the biotin-binding protein streptavidin. Streptavidin is covalently bound to the second antibody with the enzyme peroxidase or the other enzymes mentioned above. Such enzyme-streptavidin solutions are available on the market and are, for example, distributed by Calbiochem-Hoechst.

Thereafter, and in case the enzyme is a peroxidase, the streptavidin-enzyme-antibody complex is diluted with 1.2 phenylenediamine and an $H_2O_2$ solution and due to the reaction of the peroxidase with hydrogen peroxide the colourless phenylenediamine is converted to a yellow dye. By its extinction at 492 nm with reference to the wavelength of 620 nm the dye can be determined with an UV photometer. The extinction correlates with the amount of bound villin and/or fimbrin molecules as can be demonstrated in the following.

According to a fifth embodiment, villin and fimbrin in the urine can also be identified by a displacement assay. In this test reaction carriers are coated with purified villin and/or fimbrin. Thereafter a mixture consisting of a urine specimen to be examined and antibodies being specific against villin or fimbrin is added. The higher the amount of villin or fimbrin in the urine, the lower the amount of antibodies binding to those villin or fimbrin molecules already adsorbed to the reaction carrier. Thereafter the amount of bound antibodies can be quantified by directly labelling the antibodies with enzymes or radio-isotopes or by applying the other procedures as described herein.

It has to be stated once again that the quantification reactions used for the quantification complex are known. In this respect further modifications of the quantification reactions are conceivable if and to the extent it is possible to quantitatively include the bound villin or fimbrin molecules.

According to the invention a composition for carrying out the method described above is presented as well.

According to a first Embodiment A the composition comprises monoclonal or polyclonal antibodies against fimbrin and/or villin.

Preferably, antibodies already bound to a reaction carrier are introduced to the market whereby it is preferred to apply antibodies in microtiter plates. Thus a commercial unit may consist of a microtiter plate with multiple wells with each well being filled with a certain amount of antibodies against villin and/or fimbrin.

In addition to this substrate unit the composition according to the invention favourably comprises the aforementioned second antibody for generating the quantification complex. Favourably and covalently bound to this second antibody are groups of biotin. These antibodies with a biotin label may be introduced to the market either in the form of a buffered finished solution or distributed together with the buffer substance in a lyophilised form with the only need to fill the container comprising the lyophilised products with a certain quantity of water.

Such a commercial unit may furthermore—to the extent not available in the labaratory—contain concentrations of the aforementioned washing solutions as well as the quantification reagent streptavidin peroxidase, $H_2O_2$, phenylenediamine used for the quantification of the quantification complex.

Furthermore it is of advantage that for calibration of the measured values and with each substrate unit the isolated purified proteins fimbrin and/or villin are supplied, and that in a favourable quantity of about 4 $\mu g$. They are distributed in lyophilised form in a container which is filled up by the user with a certain quantity of water or urine to be examined.

According to a second Embodiment B which is based on the above described displacement assay the composition, besides the antibodies against fimbrin and/or villin as described in connection with Embodiment A above, consists of the isolated proteins villin or fimbrin.

The proteins are marketed in bound form to the reaction carrier. Each commercial unit may consist of one microtiter plate with each hole being filled with a certain quantity (for example 0.5–1 $\mu g$) of the isolated proteins villin and/or fimbrin.

In addition to this substrate unit the second composition contains the aforementioned monoclonal or polyclonal antibodies against villin or fimbrin onto which favourably and covalently biotin groups are bound. These antibodies labelled with biotin are either distributed as buffered finished solutions or in lyophilised form as described in the first embodiment.

Furthermore it is of advantage that each unit of this embodiment, for calibration purposes, also comprises the isolated proteins villin and/or fimbrin as also described in Embodiment A.

This identification kit may moreover and as described in Embodiment A comprise the aforementioned washing solutions as well as the quantification reagents.

The following example explains the invention:

Polyclonal antibodies against fimbrin and/or villin are produced according to the procedure described by Bretscher and Weber 1979, 1980, and Drenckhahn et al, 1983. Monoclonal antibodies are produced in accordance with the procedure described by Peter et al, 1985, or a monoclonal antibody against villin of Messrs. Dianova, Hamburg, is used.

These antibodies are bound to polystyrene microtiter plates obtained from Messrs. Nunc, Wiesbaden (Germany), in accordance with the procedure as described by Peter et al, 1985.

The isolated antibodies are dissolved in an immunoglobulin concentration of 5 $\mu g/ml$ in 0.2 M-carbonate buffer with a pH value of 10.6. Unpurified antiserum is conveniently diluted in the carbonate buffer at a ratio of 1:100. Hereinafter the term "antibody" is used as a term for isolated immunoglobulins and antiserum.

To provide for a sufficient binding of the antibodies to the wells of the microtiter plates 100 $\mu l$ each of the diluted antibody solution are kept in the microtiter plate wells for about 3 hours at 21° C. or twelve hours at 4° C., respectively. Thereafter the antibody solution is removed from the wells and for the saturation of empty binding sites the wells are then filled with about 400 $\mu l$ of a 1 percent by weight gelatin solution in the aforementioned carbonate buffer.

After an incubation time of one hour the gelatin solution is removed and the wells are filled with about 400 $\mu l$ washing buffer.

Said washing buffer consists of a phosphate buffered saline solution (25 mM phosphate buffer, 100 mM NaCl with a pH value of 7.4) hereinafter referred to as PPK. To this buffer solution 0.05 percent by weight of the detergent Tween 20 are added which may be obtained from Messrs. Serva, Heidelberg (Germany).

The washing buffer is changed three times in intervals of 5 minutes.

The so prepared microtiter plate may either immediately be subjected to the reaction with a urine specimen to be examined or be dried and then packed for use.

The wells of the so prepared microtiter plate are each filled with 100 μl undiluted and to be examined urine with the urine then being kept in the wells for about 1.5 hours. Thereafter the urine is removed and the wells are again incubated with 400 μl of the aforementioned washing buffer which is changed three times in intervals of 5 minutes.

Upon removal of the washing buffer the wells are each incubated again with 100 μl of the polyclonal antibodies against villin and/or fimbrin mentioned for the coating of the plates. These second antibodies are first of all covalently linked with biotin according to the method described by Heggeness, 1977 (see above). The antibodies labelled with biotin are dissolved in an immunoglobulin concentration of 10 μl/ml in a buffer consisting of 150 mM NaCl, 20 mM Tris-HCl, 0.5 mM urea and 1% gelatin and having a pH value of 7.4.

This antibody solution is then again kept in the wells for about 90 minutes. Upon removal of the second antibody solution from the wells, the wells are each filled with 400 ml PPK with 0.05 percent by weight Tween 20 which is changed three times in intervals of 5 minutes.

Thereafter the quantification reaction is made as follows.

Upon removal of the washing buffer the holes are filled with 100 μl of the aforementioned phosphate buffered saline solution (PPK, pH 7.4). This solution contains the biotin binding protein streptavidin being covalently linked with the enzyme peroxidase.

The peroxidase streptavidin is purchased from Calbiochem-Hoechst as a primary solution and applied in diluted form at 1:5,000 in PPK, pH 7.4. This streptavidin solution is kept in the holes for about 1 hour at 21° C. whereafter it is removed.

Then the wells are filled with about 400 μl of the aforementioned washing buffer (PPK, pH 7.4, 0.05 percent by weight Tween 20). This buffer solution is changed three times in intervals of 5 minutes.

Thereafter the wells are each filled with 100 μl of a phosphate citrate buffer (0.2 M disodium hydrogene phosphate, 0.1 M citric acid monohydrate with a pH of 5) which per 1 ml buffer contains 1.5 mg 1.2 phenylenediamine (obtained from Messrs. Merck) and 1 μl of a 30% $H_2O_2$ solution (distributed under the name "Perhydrol" by Messrs. Merck).

Phenylenediamine and $H_2O_2$ are added to the phosphate cicrate buffer immediately before use. Thereafter the wells are incubated with this solution for 30 minutes.

By adding 50 μl 0.5 N sulphuric acid/hole the reaction is finished.

Proportionally to the amount of the bound antibodies with biotin labels and the peroxidase labelled streptavidin molecules bound to biotin groups a yellow dye is achieved by oxidation of the colourless phenylenediamine the extinction of which at 492 nm with reference to the wavelength of 620 nm is measured in an UV photometer.

Figure 1B:
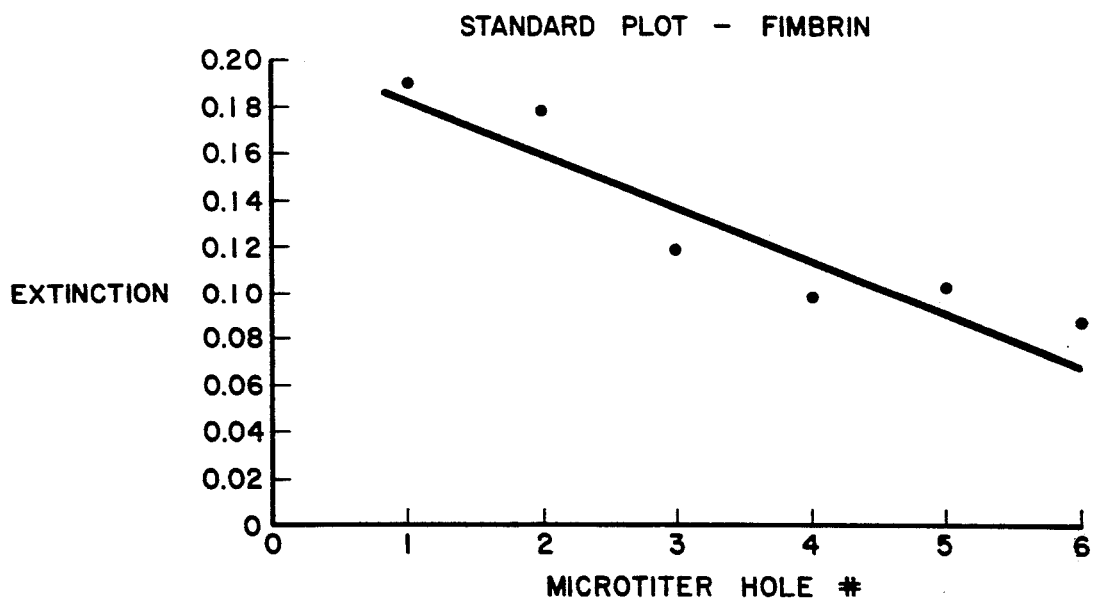

The diagram of FIG. 1 shows two standard calibration curves of villin and fimbrin for the correlation between the extinction on the one hand and the concentration of the protein on the other hand.

This calibration curve was drawn up so as to shown that defined amounts of villin (a) or fimbrin (b) were added to the urine of a healthy average person and quantified by applying the aforementioned immunologic procedure. The microtiter wells contains

1:10 μg/ml, #2:5 μg/ml, #3:2.5 μg/ml,
4:1.25 μg/ml, #5:0.625 μg/ml and
6:0.312 μg/ml protein.

These standard curves reveal both villin and fimbrin can quantitatively be identified in the urine by means of the aforementioned UV photometric method.

Figure 2:
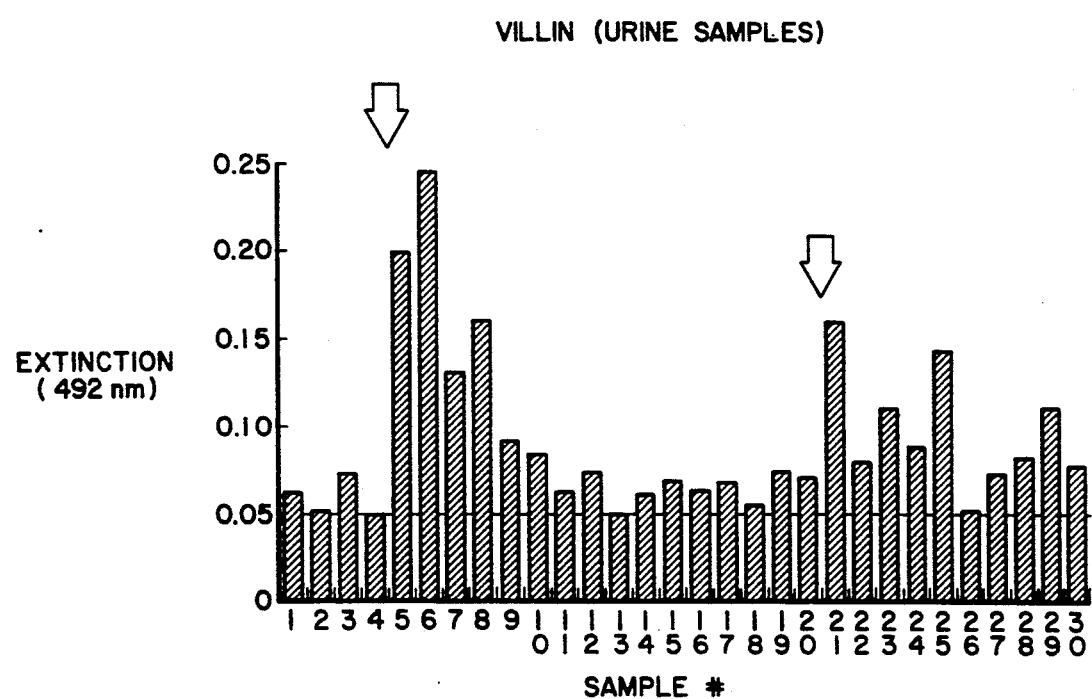

The diagram of FIG. 2 is a case study conducted over a period of 30 days (abscissa) for a patient with a transplanted kidney with the villin content of patient's urine specimen being identified per day.

FIG. 2 shows a villin concentration in patient's urine at an extinction base line of 0.05. The absolute villin concentrations in patient's urine can be taken from the calibration curve according to FIG. 1.

The arrows shown in FIG. 2 refer to rejection crises which were clinically verified by increased creatinine values and clinical symptoms and signs. The treatment during these rejection crises consisted of increased doses of immunosuppressants which resulted in a decrease of villin excretions in the urine, i.e. in a declining risk of damage to the kidney.

I claim:

1. A method for the determination of kidney damage by determining the amount of villin in a urine sample, said method comprising:
   (a) binding first antibodies to villin to a solid support,
   (b) adding a urine sample to said support so that villin in said sample specifically binds to said first antibodies,
   (c) adding second antibodies to villin, conjugated with detectable label, so as to form labeled immune complexes on said support,
   (d) determining said immune complexes, and
   (e) comparing the value of said immune complexes with the values of known amounts of villin so as to determine the amount of villin present in said sample from the group consisting of polyclonal and monoclonal antibodies.

2. A method for the determination of kidney damage by determining the amount of fimbrin in a urine sample, said method comprising:
   (a) binding first antibodies to fimbrin to a solid support,
   (b) adding a urine sample to said support so that fimbrin in said sample specifically binds to said first antibodies,
   (c) adding second antibodies to fimbrin, conjugated with detectable label, so as to form labeled immune complexes on said support,
   (d) determining said immune complexes, and
   (e) comparing the value of said immune complexes with the values of known amounts of fimbrin so as to determine the amount of fimbrin present in said sample, wherein said first and second antibodies are selected from the group consisting of polyclonal and monoclonal antibodies.

3. The method according to claims 1 or 2, wherein said first antibodies are polyclonal antibodies and said second antibodies are the same polyclonal antibodies or monoclonal antibodies.

4. The method according to claims 1 or 2, wherein said first antibodies are monoclonal antibodies and said second antibodies are polyclonal antibodies or monoclonal antibodies different from said first monoclonal antibodies.

5. A method for the determination of kidney damage by determining the amount of villin in a urine sample, said method comprising:
   (a) binding first antibodies to villin to a solid support, (b) adding a urine sample to said support so that villin in said sample specifically binds to said first antibodies, (c) adding second antibodies to villin so as to form immune complexes on said support, (d) determining said immune complexes by means of third antibodies, conjugated with detectable label, directed against said second antibodies but not said first antibodies.

(e) comparing the value of said immune complexes with the values of known amounts of villin so as to determine the amount of villin present in said sample, wherein said first and second antibodies are selected from the group consisting of polyclonal and monoclonal antibodies.

6. A method for the determination of kidney damage by determining the amount of fimbrin in a urine sample, said method comprising:

(a) binding first antibodies to fimbrin to a solid support, (b) adding a urine sample to said support so that fimbrin in said sample specifically binds to said first antibodies, (c) adding second antibodies to fimbrin so as to form immune complexes on said support, (d) determining said immune complexes by means of third antibodies, conjugated with detectable label, directed against said second antibodies but not said first antibodies.

(e) comparing the value of said immune complexes with the values of known amounts of fimbrin so as to determine the amount of fimbrin present in said sample, wherein said first and second antibodies are selected from the group consisting of polyclonal and monoclonal antibodies.

7. A method for the determination of kidney damage by determining the amount of villin in a urine sample, said method comprising:

(a) binding villin to a solid support, (b) adding first antibodies to villin, conjugated to detectable label, to an urine sample so that villin in said sample specifically binds to said first antibodies to form a urine-antibody solution, (c) adding said solution to said support so that said first antibodies which are unbound after step (b) specifically bind to said solid support, (d) determining said first antibodies, and (e) comparing the value of said first antibodies with the values of known amounts of first antibodies so as to determine the amount of villin present in said sample, wherein said first antibodies are selected from the group consisting of polyclonal and monoclonal antibodies.

8. A method for the determination of kidney damage by determining the amount of fimbrin in a urine sample, said method comprising:

(a) binding fimbrin to a solid support, (b) adding first antibodies to fimbrin, conjugated to detectable label, to an urine sample so that fimbrin in said sample specifically binds to said first antibodies to form a urine-antibody solution, (c) adding said solution to said support so that said first antibodies which are unbound after step (b) specifically bind to said solid support, (d) determining said first antibodies, and (e) comparing the value of said first antibodies with the values of known amounts of first antibodies so as to determine the amount of fimbrin present in said sample, wherein said first antibodies are selected from the group consisting of polyclonal and monoclonal antibodies.

9. A method for the determination of kidney damage by determining the amount of villin in a urine sample, said method comprising:

(a) binding villin to a solid support, (b) adding first antibodies to villin to an urine sample so that villin in said sample specifically binds to said first antibodies to form a urine-antibody solution, (c) adding said solution to said support so that said first antibodies which are unbound after step (b) specifically bind to said solid support, (d) adding second antibodies to said first antibodies, conjugated with detectable label, so that said second antibodies specifically bind to said first antibodies bound to said solid support, (e) determining said second antibodies, and (f) comparing the value of said second antibodies with the values of known amounts of second antibodies so as to determine the amount of villin present in said sample, wherein said first and second antibodies are selected from the group consisting of polyclonal and monoclonal antibodies.

10. A method for the determination of kidney damage by determining the amount of fimbrin in a urine sample, said method comprising:

(a) binding fimbrin to a solid support, (b) adding first antibodies to fimbrin to an urine sample so that fimbrin in said sample specifically binds to said first antibodies to form a urine-antibody solution (c) adding said solution to said support so that said first antibodies which are unbound after step (b) specifically bind to said solid support, (d) adding second antibodies to said first antibodies, conjugated with detectable label, so that said second antibodies specifically bind to said first antibodies bound to said solid support, (e) determining said second antibodies, and (f) comparing the value of said second antibodies with the values of known amounts of second antibodies so as to determine the amount of fimbrin present in said sample, wherein said first and second antibodies are selected from the group consisting of polyclonal and monoclonal antibodies.

* * * * *